United States Patent [19]

Cherpeck

[11] Patent Number: 5,709,720
[45] Date of Patent: Jan. 20, 1998

[54] AROMATIC ETHERS OF POLYALKYLPHENOXYALKANOLS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 746,098

[22] Filed: Nov. 7, 1996

[51] Int. Cl.$^6$ ................ C10L 1/22; C10L 1/18
[52] U.S. Cl. ................ 44/413; 44/424; 44/427; 44/442; 44/447; 564/305; 564/389; 564/441; 568/630; 568/631; 568/650; 568/652
[58] Field of Search ................ 44/413, 427, 424, 44/442, 447; 564/389; 568/630, 631

[56] References Cited

U.S. PATENT DOCUMENTS

| | | | |
|---|---|---|---|
| 2,714,607 | 8/1955 | Matter | 260/471 |
| 3,149,933 | 9/1964 | Ley et al. | 44/75 |
| 3,434,814 | 3/1969 | Dubeck et al. | 44/69 |
| 3,849,085 | 11/1974 | Kreuz et al. | 44/78 |
| 4,134,846 | 1/1979 | Machleder et al. | 252/51.5 A |
| 4,320,021 | 3/1982 | Lange | 252/51.5 R |
| 4,347,148 | 8/1982 | Davis | 252/51.5 |
| 4,386,939 | 6/1983 | Lange | 44/63 |
| 5,090,914 | 2/1992 | Reardan et al. | 435/188 |
| 5,211,721 | 5/1993 | Sung et al. | 44/389 |
| 5,409,507 | 4/1995 | Cherpeck | 44/399 |
| 5,441,544 | 8/1995 | Cherpeck | 44/384 |
| 5,482,523 | 1/1996 | Cherpeck | 44/391 |
| 5,516,342 | 5/1996 | Cherpeck | 44/347 |
| 5,637,119 | 6/1997 | Cherpeck | 44/413 |

*Primary Examiner*—Ellen M. McAvoy
*Attorney, Agent, or Firm*—Claude J. Caroli

[57] ABSTRACT

Aromatic ethers of polyalkylphenoxyalkanols having the formula:

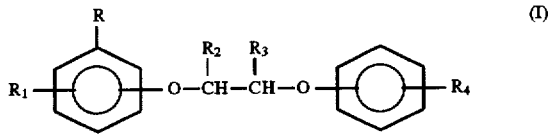

(I)

or a fuel soluble salt thereof, wherein R is hydroxy, nitro or —$(CH_2)_x$-$NR_5R_6$, wherein $R_5$ and $R_6$ are independently hydrogen or lower alkyl having 1 to carbon atoms, and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

The compounds of formula I are useful as fuel additives for the prevention and control of engine deposits.

54 Claims, No Drawings

AROMATIC ETHERS OF POLYALKYLPHENOXYALKANOLS AND FUEL COMPOSITIONS CONTAINING THE SAME

BACKGROUND OF THE INVENTION

1. Field of the Invention

This invention relates to aromatic ethers of polyalkylphenoxyalkanols and derivatives thereof. In a further aspect, this invention relates to the use of these compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Similarly, U.S. Pat. No. 3,149,933, issued Sep. 22, 1964 to K. Ley et al., discloses hydrocarbon-substituted amino phenols as stabilizers for liquid fuels.

U.S. Pat. No. 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

More recently, certain poly(oxyalkylene) esters have been shown to reduce engine deposits when used in fuel compositions. U.S. Pat. No. 5,211,721, issued May 18, 1993 to R. L. Sung et al., for example, discloses an oil soluble polyether additive comprising the reaction product of a polyether polyol with an acid represented by the formula RCOOH in which R is a hydrocarbyl radical having 6 to 27 carbon atoms. The poly(oxyalkylene) ester compounds of this patent are taught to be useful for inhibiting carbonaceous deposit formation, motor fuel hazing, and as ORI inhibitors when employed as soluble additives in motor fuel compositions.

Poly(oxyalkylene) esters of amino- and nitrobenzoic acids are also known in the art. For example, U.S. Pat. No. 2,714,607, issued Aug. 2, 1955 to M. Matter, discloses polyethoxy esters of aminobenzoic acids, nitrobenzoic acids and other isocyclic acids. These polyethoxy esters are taught to have excellent pharmacological properties and to be useful as anesthetics, spasmolytics, analeptics and bacteriostatics.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes.

My prior U.S. Pat. No. 5,409,507, issued Apr. 25, 1995, discloses certain poly(oxyalkylene) nitro and aminoaromatic ethers having from 5 to 100 oxyalkylene units and teaches the use of such compounds as fuel additives for the prevention and control of engine deposits.

Similarly, my prior U.S. Pat. No. 5,441,544, issued Aug. 15, 1995, discloses certain poly(oxyalkylene) aromatic ethers having from 5 to 100 oxyalkylene units which are useful as fuel additives to control engine deposits, wherein the aromatic ring may be substituted with a thioether, a sulfoxide, a sulfone, a sulfonic acid, a sulfonamide, a nitrile, a carboxylic acid or ester, or a carboxamide.

In addition, my prior U.S. Pat. No. 5,516,342, issued May 14, 1996, discloses a fuel additive composition containing the combination of a poly(oxyalkylene) hydroxyaromatic ether having from 5 to 100 oxyalkylene units and an aliphatic amine.

Moreover, my prior U.S. Pat. No. 5,482,523, issued Jan. 9, 1996, discloses a deposit control additive for fuels which is a Mannich condensation product prepared by the condensation of a poly(oxyalkylene) hydroxyaromatic ether with an aldehyde and a nitrogen base selected from ammonia, a lower alkylamine and a polyamine.

SUMMARY OF THE INVENTION

I have now discovered certain aromatic ethers of polyalkylphenoxyalkanols which provide excellent control of engine deposits, especially intake valve deposits, when employed as fuel additives in fuel compositions.

The compounds of the present invention include those having the following formula and fuel soluble salts thereof:

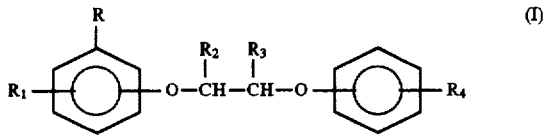
(I)

wherein R is hydroxy, nitro or —$(CH_2)_x$—$NR_5R_6$, wherein $R_5$ and $R_6$ are independently hydrogen or lower alkyl having 1 to 6 carbon atoms and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

The present invention further provides a fuel composition comprising a major amount of hydrocarbons boiling in the gasoline or diesel range and a deposit-controlling effective amount of a compound of the present invention.

The present invention additionally provides a fuel concentrate comprising an inert stable oleophilic organic solvent boiling in the range of from about 150° F. to 400° F. and from about 10 to 70 weight percent of a compound of the present invention.

Among other factors, the present invention is based on the surprising discovery that certain aromatic ethers of polyalkylphenoxyalkanols provide excellent control of engine deposits, especially on intake valves, when employed as additives in fuel compositions.

DETAILED DESCRIPTION OF THE INVENTION

Based on performance (e.g., deposit control), handling properties and performance/cost effectiveness, the preferred compounds of the invention are those wherein R is nitro, amino, N-alkylamino, or —$CH_2NH_2$ (aminomethyl). More preferably, R is a nitro, amino or —$CH_2NH_2$ group. Most preferably, R is an amino or —$CH_2NH_2$ group, especially amino. Preferably, $R_1$ is hydrogen, hydroxy, nitro or amino. More preferably, $R_1$ is hydrogen or hydroxy. Most preferably, $R_1$ is hydrogen. Preferably, $R_4$ is a polyalkyl group having an average molecular weight in the range of about 500 to 3,000, more preferably about 700 to 3,000, and most preferably about 900 to 2,500. Preferably, the compound has a combination of preferred substituents.

Preferably, one of $R_2$ and $R_3$ is hydrogen or lower alkyl of 1 to 4 carbon atoms, and the other is hydrogen. More preferably, one of $R_2$ and $R_3$ is hydrogen, methyl or ethyl, and the other is hydrogen. Most preferably, $R_2$ is hydrogen, methyl or ethyl, and $R_3$ is hydrogen.

When R and/or $R_1$ is an N-alkylamino group, the alkyl group of the N-alkylamino moiety preferably contains 1 to 4 carbon atoms. More preferably, the N-alkylamino is N-methylamino or N-ethylamino.

Similarly, when R and/or $R_1$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A further preferred group of compounds are those wherein R is amino, nitro, or —$CH_2NH_2$ and $R_1$ is hydrogen or hydroxy. A particularly preferred group of compounds are those wherein R is amino, $R_1$, $R_2$ and $R_3$ are hydrogen, and $R_4$ is a polyalkyl group derived from polyisobutene.

It is preferred that the R substituent is located at the meta or, more preferably, the para position of the phenoxy moiety, i.e., para or meta relative to the ether oxygen. When $R_1$ is a substituent other than hydrogen, it is particularly preferred that this $R_1$ group be in a meta or para position relative to the ether oxygen and in an ortho position relative to the R substituent. Further, in general, when $R_1$ is other than hydrogen, it is preferred that one of R or $R_1$ is located para to the ether oxygen and the other is located meta to the ether oxygen. Similarly, it is preferred that the $R_4$ substituent on the other phenyl ring is located para or meta, more preferably para, relative to the ether linking group.

The compounds of the present invention will generally have a sufficient molecular weight so as to be non-volatile at normal engine intake valve operating temperatures (about 200° C.–250° C.). Typically, the molecular weight of the compounds of this invention will range from about 700 to about 3,500, preferably from about 700 to about 2,500.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

When the R or $R_1$ substituent is a hydroxy group, suitable salts can be obtained by deprotonation of the hydroxy group with a base. Such salts include salts of alkali metals, alkaline earth metals, ammonium and substituted ammonium salts. Preferred salts of hydroxy-substituted compounds include alkali metal, alkaline earth metal and substituted ammonium salts.

DEFINITIONS

As used herein, the following terms have the following meanings unless expressly stated to the contrary.

The term "amino" refers to the group: —$NH_2$.

The term "N-alkylamino" refers to the group: —$NHR_a$ wherein $R_a$ is an alkyl group. The term "N,N-dialkylamino" refers to the group: —$NR_bR_c$, wherein $R_b$ and $R_c$ are alkyl groups.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The term "fuel" or "hydrocarbon fuel" refers to normally liquid hydrocarbons having boiling points in the range of gasoline and diesel fuels.

GENERAL SYNTHETIC PROCEDURES

The polyalkylphenoxyalkyl aromatic ethers of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art.

Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the aromatic ethers of this invention having an amino group on the aromatic moiety will generally be prepared from the corresponding nitro derivative. Accordingly, in many of the following procedures, a nitro group will serve as a protecting group for the amino moiety.

Moreover, the compounds of this invention having a —CH$_2$NH$_2$ group on the aromatic moiety will generally be prepared from the corresponding cyano derivative, —CN. Thus, in many of the following procedures, a cyano group will serve as a protecting group for the —CH$_2$NH$_2$ moiety.

SYNTHESIS

The polyalkylphenoxyalkyl aromatic ethers of the present invention may be prepared by a process which initially involves hydroxyalkylation of a polyalkylphenol of the formula:

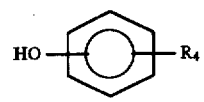

wherein R$_4$ is as defined herein, with an alkylene carbonate of the formula:

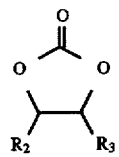

wherein R$_2$ and R$_3$ are as defined herein, in the presence of a catalytic amount of an alkali metal hydride or hydroxide, or alkali metal salt, to provide a polyalkylphenoxyalkanol of the formula:

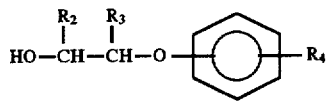

wherein R$_2$, R$_3$ and R$_4$ are as defined herein.

The polyalkylphenols of formula II are well known materials and are typically prepared by the alkylation of phenol with the desired polyolefin or chlorinated polyolefin. A further discussion of polyalkylphenols can be found, for example, in U.S. Pat. No. 4,744,921 and U.S. Pat. No. 5,300,701.

Accordingly, the polyalkylphenols of formula II may be prepared from the corresponding olefins by conventional procedures. For example, the polyalkylphenols of formula II above may be prepared by reacting the appropriate olefin or olefin mixture with phenol in the presence of an alkylating catalyst at a temperature of from about 25° C. to 150° C., and preferably 30° C. to 100° C., either neat or in an essentially inert solvent at atmospheric pressure. A 4 preferred alkylating catalyst is boron trifluoride. Molar ratios of reactants may be used. Alteratively, molar excesses of phenol can be employed, i.e., 2 to 3 equivalents of phenol for each equivalent of olefin with unreacted phenol recycled. The latter process maximizes monoalkylphenol. Examples of inert solvents include heptane, benzene, toluene, chlorobenzene and 250 thinner which is a mixture of aromatics, paraffins and naphthenes.

The polyalkyl substituent on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkylphenols are polyisobutenes which comprise at least about 20% of the more reactive methylvinylidene isomer, preferably at least 50% and more preferably at least 70%. Suitable polyisobutenes include those prepared using BF$_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1300 and a methylvinylidene content of about 74%, and Ultravis 10, a polyisobutene having a number average molecular weight of about 950 and a methylvinylidene content of about 76%, both available from British Petroleum.

The alkylene carbonates of formula III are known compounds which are available commercially or can be readily prepared using conventional procedures. Suitable alkylene carbonates include ethylene carbonate, propylene carbonate, 1,2-butylene carbonate, 2,3-butylene carbonate, and the like. A preferred alkylene carbonate is ethylene carbonate.

The catalyst employed in the reaction of the polyaklyphenol and alkylene carbonate may be any of the well known hydroxyalkylation catalysts. Typical hydroxyalkylation catalysts include alkali metal hydrides, such as lithium hydride, sodium hydride and potassium hydride, alkali metal hydroxides, such as sodium hydroxide and potassium hydroxide, and alkali metal salts, for example, alkali metal halides, such as sodium chloride and potassium chloride, and alkali metal carbonates, such as sodium carbonate and potassium carbonate. The amount of catalyst employed will generally range from about 0.01 to 1.0 equivalent, preferably from about 0.05 to 0.3 equivalent.

The polyalkylphenol and alkylene carbonate are generally reacted in essentially equivalent amounts in the presence of the hydroxyalkylation catalyst at a temperature in the range of about 100° C. to 210° C., and preferably from about 150° C. to about 170° C. The reaction may take place in the presence or absence of an inert solvent.

The time of reaction will vary depending on the particular alkylphenol and alkylene carbonate reactants, the catalyst used and the reaction temperature. Generally, the reaction time will range from about two hours to about five hours. The progress of the reaction is typically monitored by the evolution of carbon dioxide. At the completion of the reaction, the polyalkylphenoxyalkanol product is isolated using conventional techniques.

The hydroxyalkylation reaction of phenols with alkylene carbonates is well known in the art and is described, for example, in U.S. Pat. Nos. 2,987,555; 2,967,892; 3,283,030 and 4,341,905.

Alternatively, the polyalkylphenoxyalkanol product of formula IV may be prepared by reacting the polyalkylphenol of formula II with an alkylene oxide of the formula:

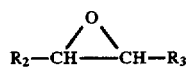

(V)

wherein $R_2$ and $R_3$ are as defined herein, in the presence of a hydroxyalkylation catalyst as described above.

Suitable alkylene oxides of formula V include ethylene oxide, propylene oxide, 1,2-butylene oxide, 2,3-butylene oxide, and the like. A preferred alkylene oxide is ethylene oxide.

In a manner similar to the reaction with alkylene carbonate, the polyalkylphenol and alkylene oxide are reacted in essentially equivalent or equimolar amounts in the presence of 0.01 to 1.0 equivalent of a hydroxyalkylation catalyst, such as sodium or potassium hydride, at a temperature in the range of about 30° C. to about 150° C., for about 2 to about 24 hours. The reaction may be conducted in the presence or absence of a substantially anhydrous inert solvent. Suitable solvents include toluene, xylene, and the like. Generally, the reaction conducted at a pressure sufficient to contain the reactants and any solvent present, typically at atmospheric or higher pressure. Upon completion of the reaction, the polyalkylphenoxyalkanol is isolated by conventional procedures.

The polyalkylphenoxyalkanol of formula IV is then deprotonated with a suitable base to provide the metal salt of formula IVA, which is subsequently reacted with a substituted phenyl halide of formula VI to provide the aromatic ether compounds of formula I. This reaction can be represented as follows:

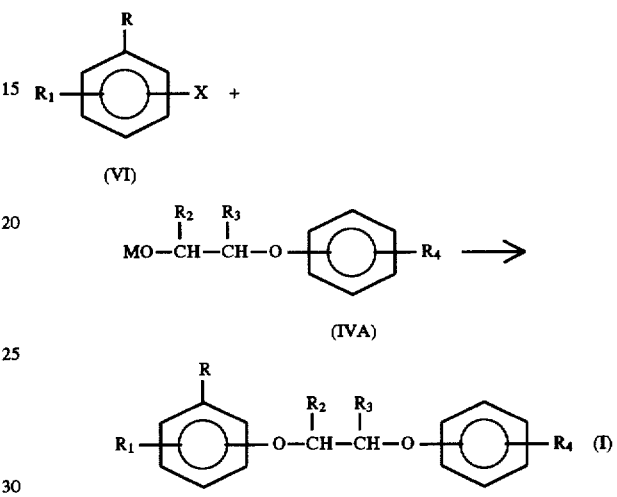

wherein R, $R_1$, $R_2$, $R_3$ and $R_4$ are as defined herein, M is a metal cation, such as lithium, sodium or potassium, and X is a halogen, such as fluoro, chloro, or bromo, and wherein any hydroxy or amino substituent on the substituted phenyl halide of formula VI is preferably protected with a suitable protecting group, for example, a benzyl or nitro group, respectively. Moreover, a —$CH_2NH_2$ substituent on the aromatic ring will preferably be protected by the use of a cyano group, CN.

Generally, the deprotonation reaction will be effected by contacting the polyalkylphenoxyalkanol of formula IV with a strong base, such as sodium hydride, potassium hydride, sodium amide, potassium hydroxide, and the like, in an inert solvent, such as toluene, xylene, and the like, under substantially anhydrous conditions at a temperature in the range of about −10° C. to about 120° C. for about 0.25 to about 3 hours. This reaction may also be promoted by copper salts. See, for example, J. Lindley, Tetrahedron, Vol. 40, pp. 1433–1456, 1984.

The metal salt of formula IVA is generally not isolated, but is reacted in situ with about 0.8 to about 2.0 molar equivalents of the substituted and suitably protected phenyl halide of formula VI. Typically, this reaction is conducted in a substantially anhydrous inert solvent at a temperature in the range of about 30° C. to about 160° C. for about 0.5 to about 48 hours. Suitable solvents for this reaction include toluene, xylene, tetraahydrofuran, and the like. The reaction will generally be conducted at a pressure sufficient to contain the reactants and the solvent, preferably at atmospheric or ambient pressure.

The substituted phenyl halides of formula VI are generally known compounds and can be prepared from known compounds using conventional procedures or obvious modifications thereof. Representative phenyl halides which may be used as starting materials and, if necessary, when suitably protected, include, for example, 4-fluoronitrobenzene, 4-bromonitrobenzene, 3-fluoronitrobenzene, 3-bromonitrobenzene, 2-hydroxy-4-fluoronitrobenzene, 2-hydroxy-4-bromonitrobenzene, 2-nitro-4-fluorophenol, and 2-nitro-4-bromophenol. When the R substituent is —$CH_2$—$NR_5R_6$, suitable starting materials include, for example, 4-fluorocyanobenzene, 4-bromocyanobenzene, 3-fluorocyanobenzene, and 3-bromocyanobenzene.

Preferred substituted phenyl halides include 4-fluoronitrobenzene, 2-hydroxy-4-fluoronitrobenzene, and 4-fluorocyanobenzene.

When the substituted phenyl halides of formula VI contain a hydroxyl group, protection of the aromatic hydroxyl groups may be accomplished using well-known procedures. The choice of a suitable protecting group for a particular hydroxy-substituted phenyl halide will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein.

After completion of the etherification reaction, deprotection of the aromatic hydroxyl group can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

When the substituted phenyl halides of formula VI have a free amino group (—$NH_2$) on the phenyl moiety, it is generally desirable to employ the corresponding nitro compound (i.e., where R and/or $R_1$ is a nitro group) and then reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron and the like, in the presence of an acid, such as dilute hydrochloric acid. Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate and the like. Hydrogenation of aromatic nitro groups is discussed in further detail in, for example, P. N. Rylander, *Catalytic Hydrogenation in Organic Synthesis*, pp. 113–137, Academic Press (1979); and *Organic Synthesis, Collective Vol. 1*, Second Edition, pp. 240–241, John Wiley & Sons, Inc. (1941); and references cited therein.

Likewise, when the substituted phenyl halides of formula VI contain a —$CH_2NH_2$ group on the phenyl moiety, it is generally desirable to employ the corresponding cyano compounds (i.e., where R and/or $R_1$ is a —CN group), and then reduce the cyano group to a —$CH_2NH_2$ group using conventional procedures. Aromatic cyano groups may be reduced to —$CH_2NH_2$ groups using procedures well known in the art. For example, aromatic cyano groups may be reduced under catalytic hydrogenation conditions similar to those described above for reduction of aromatic nitro groups to amino groups. Thus, this reaction is typically conducted using about 1 to 4 atmospheres of hydrogen and a platinum or palladium catalyst, such as palladium on carbon. Another suitable catalyst is a Lindlar catalyst, which is palladium on calcium carbonate. The hydrogenation may be carried out at temperatures of about 0° C. to about 100° C. for about 1 to 24 hours in an inert solvent such as ethanol, ethyl acetate, and the like. Hydrogenation of aromatic cyano groups is further discussed in the references cited above for reduction of aromatic nitro groups.

FUEL COMPOSITIONS

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the compounds of this invention in hydrocarbon fuel will range from about 50 to about 2500 parts per million (ppm) by weight, preferably from 75 to 1,000 ppm. When other deposit control additives are present, a lesser amount of the present additive may be used.

The compounds of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, hydrocarbyl poly(oxyalkylene) aminocarbamates, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the aromatic ethers of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis, and polyesters, such as those described, for example, in U.S. Pat. Nos. 3,756,793 to Robinson and 5,004,478 to Vogel et al., and in European Patent Application Nos. 356,726, published Mar. 7, 1990, and 382,159, published Aug. 16, 1990.

These carrier fluids are believed to act as a carrier for the fuel additives of the present invention and to assist in removing and retarding deposits. The carrier fluid may also exhibit synergistic deposit control properties when used in combination with an aromatic ether of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

PREPARATIONS AND EXAMPLES

A further understanding of the invention can be had in the following nonlimiting Examples. Wherein unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (rid), triplets (t), double triplets (dt), quartets (q), and multiplets (m), and cps refers to cycles per second.

Example 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 Polyisobutene (molecular weight 950, 76% methylvinylidene, available from British Petroleum) was dissolved in 1,863 milliliters of hexane. The polyisobutene was added to the reaction at a rate to maintain the temperature between 22° C.–27° C. The reaction mixture was stirred for 16 hours at room temperature. Then, 400 milliliters of concentrated ammonium hydroxide was added, followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane:ethylacetate:ethanol (93:5:2).

Example 2

Preparation of

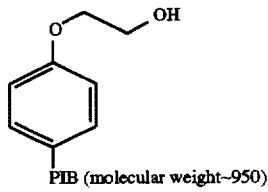

PIB (molecular weight–950)

1.1 grams of a 35 weight percent dispersion of potassium hydride in mineral oil and 4-polyisobutyl phenol (99.7 grams, prepared as in Example 1) were added to a flask equipped with a magnetic stirrer, reflux condensor, nitrogen inlet and thermometer. The reaction was heated at 130° C. for one hour and then cooled to 100° C. Ethylene carbonate (8.6 grams) was added and the mixture was heated at 160° C. for 16 hours. The reaction was cooled to room temperature and one milliliter of isopropanol was added. The reaction was diluted with one liter of hexane, washed three times with water and once with brine. The organic layer was dried over anhydrous magnesium sulfate, filtered and the solvents removed in vacuo to yield 98.0 grams of the desired product as a yellow oil.

Example 3

Preparation of

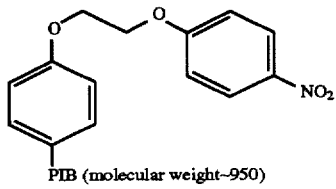

PIB (molecular weight–950)

To a flask equipped with a magnetic stirrer, reflux condensor, septa and nitrogen inlet was added potassium hydride (1.7 grams, 35 weight percent dispersion in mineral oil) and anhydrous tetrahydrofuran (50 mL). The contents of the flask were cooled to 0° C. with an ice bath. The product from Example 2 (15.0 grams, dissolved in 100 mL of anhydrous tetrahydrofuran) was added dropwise. The mixture was stirred at room temperature until the potassium hydride was completely reacted. 1-Fluoro-4-nitrobenzene (2.2 grams) was added all at once. The reaction was refluxed for 16 hours, cooled to room temperature and a few drops of isopropyl alcohol were added. Brine (300 mL) was added and the aqueous phase was extracted with hexane (3×300 mL). The combined hexane layers were dried over anhydrous magnesium sulfate, filtered and concentrated in vacuo to yield 18.6 grams of the desired product as a yellow oil. $^1$H NMR (CDCl$_3$) δ 8.2 (d, 2H), 7.25 (d, 2H), 7.0 (d, 2H), 6.85 (d, 2H), 4.25–4.45 (m, 4H), 0.7–1.8 (m, 137H).

Example 4

Preparation of

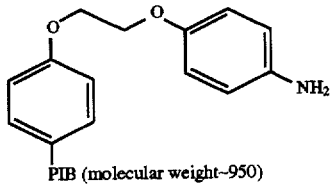

A solution of 18.6 grams of the product from Example 3 in 200 mL of ethyl acetate containing 1.0 grams of 10% palladium on charcoal was hydrogenolyzed at 35–40 psi for 16 hours on a Parr low-pressure hydrogenator. Catalyst filtration and removal of solvent in vacuo yielded 16.9 grams of the desired product as a brown oil. The oil was chromatographed on silica gel, eluting with hexane/ethyl acetate (95:5) followed by hexane/diethyl ether/isopropylamine (49:49:2) to afford 8.8 grams of the desired product as a brown oil. $^1$H NMR (CDCl$_3$) δ 7.25 (d, 2H), 6.9 (d, 2H), 6.8 (d, 2H), 6.65 (d, 2H), 4.25 (s, 4H), 3.5 (bs, 2H), 0.7–1.8 (m, 137H).

Example 5

Preparation of

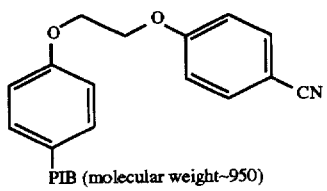

To a flask equipped with a magnetic stirrer, reflux condensor, septa and nitrogen inlet was added potassium hydride (1.1 grams, 35 weight percent dispersion in mineral oil) and anhydrous tetrahydrofuran (50 mL). The contents of the flask were cooled to 0° C. with an ice bath. The product from Example 2 (10.0 grams, dissolved in 50 mL of anhydrous tetrahydrofuran) was added dropwise. The mixture was stirred at room temperature until the potassium hydride was completely reacted. 4-Fluorobenzonitrile (1.3 grams) was added all at once. The reaction was refluxed for 16 hours, cooled to room temperature and a few drops of isopropyl alcohol were added. Brine (300 mL) was added and the aqueous phase was extracted with hexane (3×300 mL). The combined hexane layers were dried over anhydrous magnesium sulfate, filtered and concentrated in vacuo to yield 11.6 grams of the desired product as a yellow oil. $^1$H NMR (CDCl$_3$) δ 7.6 (d, 2H), 7.3 (d, 2H), 7.0(d, 2H), 6.85 (d, 2H), 4.3 (s, 4H), 0.7–1.8 (m, 137H).

Example 6

Preparation of

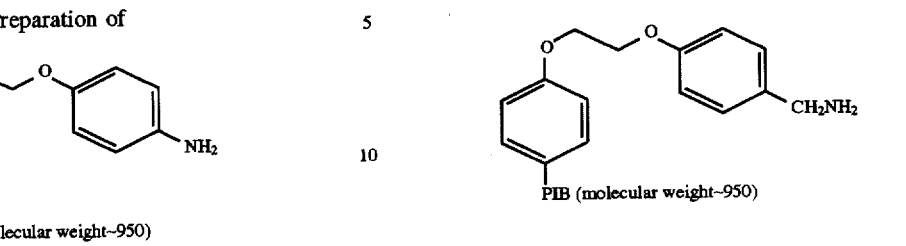

A solution of 17.5 grams of the product from Example 5 in 100 mL of ethyl acetate and 100 mL of acetic acid containing 1.0 gram of 10% palladium on charcoal was hydrogenolyzed at 35–40 psi for 16 hours on a Parr low-pressure hydrogenator. Catalyst filtration and removal of residual acetic acid with toluene in vacuo yielded 13.7 grams of the desired product as a black oil. The oil was chromatographed on silica gel, eluting with hexane/ethyl acetate (90:10) followed by hexane/diethyl ether/methanol/isopropylamine (40:40:15:5) to afford 5.8 grams of the desired product as a black oil. $^1$H NMR (CDCl$_3$) δ 7.15–7.3 (m, 4H), 6.75–6.95 (m, 4H), 4.3 (s, 4H), 3.85 (s, 2H), 2.15 (bs, 2H), 0.7–1.8 (m, 137H).

Example 7

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 400 BTC; engine speed is 1800 rpm; the crankcase oil is a commercial 30 W oil.

The amount of carbonaceous deposit in milligrams on the intake valves is reported for each of the test compounds in Table I and Table II.

TABLE I

| Sample[1] | Intake Valve Deposit Weight (in milligrams) | | |
|---|---|---|---|
| | Run 1 | Run 2 | Average |
| Base Fuel | 337.7 | 351.0 | 344.4 |
| Example 4 | 14.2 | 12.7 | 13.5 |

[1] At 150 parts per million actives (ppma).

15

TABLE II

| Sample[1] | Intake Valve Deposit Weight (in milligrams) | | |
|---|---|---|---|
| | Run 1 | Run 2 | Average |
| Base Fuel | 297.5 | 291.4 | 294.5 |
| Example 6 | 22.2 | 33.6 | 27.9 |

[1]At 125 parts per million actives (ppma).

The base fuel employed in the above single-cylinder engine tests was a regular octane unleaded gasoline containing no fuel detergent. The test compounds were admixed with the base fuel to give the concentrations indicated in the tables.

The data in Table I and Table II illustrates the significant reduction in intake valve deposits provided by the aromatic ethers of the polyalkylphenoxyalkanols of the present invention (Examples 4 and 6) compared to the base fuel.

What is claimed is:

1. A compound of the formula:

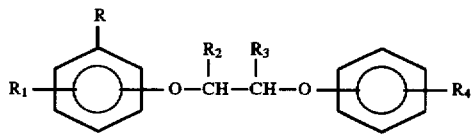

or a fuel soluble salt thereof, wherein R is hydroxy, nitro or —$(CH_2)_x$—$NR_5R_6$, wherein $R_5$ and $R_6$ are independently hydrogen or lower alkyl having 1 to 6 carbon atoms, and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

2. The compound according to claim 1, wherein R is nitro, amino or —$CH_2NH_2$.

3. The compound according to claim 2, wherein R is amino, or —$CH_2NH_2$.

4. The compound according to claim 3, wherein R is amino.

5. The compound according to claim 1, wherein $R_1$ is hydrogen, hydroxy, nitro or amino.

6. The compound according to claim 5, wherein $R_1$ is hydrogen or hydroxy.

7. The compound according to claim 6, wherein $R_1$ is hydrogen.

8. The compound according to claim 1, wherein one of $R_2$ and $R_3$ is hydrogen or lower alkyl of 1 to 4 carbon atoms, and the other is hydrogen.

9. The compound according to claim 8, wherein one of $R_2$ and $R_3$ is hydrogen, methyl or ethyl, and the other is hydrogen.

10. The compound according to claim 9, wherein $R_2$ is hydrogen, methyl or ethyl, and $R_3$ is hydrogen.

11. The compound according to claim 1, wherein $R_4$ is a polyalkyl group having an average molecular weight in the range of about 500 to 3,000.

12. The compound according to claim 11, wherein $R_4$ is a polyalkyl group having an average molecular weight in the range of about 700 to 3,000.

16

13. The compound according to claim 12, wherein $R_4$ is a polyalkyl group having an average molecular weight in the range of about 900 to 2,500.

14. The compound according to claim 1, wherein $R_4$ is a polyalkyl group derived from polypropylene, polybutene, or a polyalphaolefin oligomer of 1-octene or 1-decene.

15. The compound according to claim 14, wherein $R_4$ is a polyalkyl group derived from polyisobutene.

16. The compound according to claim 15, wherein the polyisobutene contains at least about 20% of a methylvinylidene isomer.

17. The compound according to claim 1, wherein R is amino, $R_1$, $R_2$ and $R_3$ are hydrogen and $R_4$ is a polyalkyl group derived from polyisobutene.

18. A fuel composition comprising a major amount of hydrocarbons boiling in the gasoline or diesel range and an effective deposit-controlling amount of a compound of the formula:

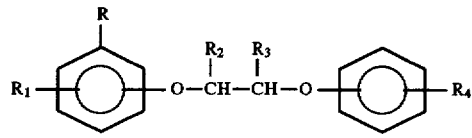

or a fuel soluble salt thereof, wherein R is hydroxy, nitro or —$(CH_2)_x$—$NR_5R_6$, wherein $R_5$ and $R_6$ are independently hydrogen or lower alkyl having 1 to 6 carbon atoms, and x is 0 or 1;

$R_1$ is hydrogen, hydroxy, nitro or —$NR_7R_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

19. The fuel composition according to claim 18, wherein R is nitro, amino or —$CH_2NH_2$.

20. The fuel composition according to claim 19, wherein R is amino, or —$CH_2NH_2$.

21. The fuel composition according to claim 20, wherein R is amino.

22. The fuel composition according to claim 18, wherein $R_1$ is hydrogen, hydroxy, nitro or amino.

23. The fuel composition according to claim 22, wherein $R_1$ is hydrogen or hydroxy.

24. The fuel composition according to claim 23, wherein $R_1$ is hydrogen.

25. The fuel composition according to claim 18, wherein one of $R_2$ and $R_3$ is hydrogen or lower alkyl of 1 to 4 carbon atoms, and the other is hydrogen.

26. The fuel composition according to claim 25, wherein one of $R_2$ and $R_3$ is hydrogen, methyl or ethyl, and the other is hydrogen.

27. The fuel composition according to claim 26, wherein $R_2$ is hydrogen, methyl or ethyl, and $R_3$ is hydrogen.

28. The fuel composition according to claim 18, wherein $R_4$ is a polyalkyl group having an average molecular weight in the range of about 500 to 3,000.

29. The fuel composition according to claim 28, wherein $R_4$ is a polyalkyl group having an average molecular weight in the range of about 700 to 3,000.

30. The fuel composition according to claim 29, wherein $R_4$ is a polyalkyl group having an average molecular weight in the range of about 900 to 2,500.

31. The fuel composition according to claim 18, wherein $R_4$ is a polyalkyl group derived from polypropylene, polybutene, or a polyalphaolefin oligomer of 1-octene or 1-decene.

32. The fuel composition according to claim 31, wherein $R_4$ is a polyalkyl group derived from polyisobutene.

33. The fuel composition according to claim 32, wherein the polyisobutene contains at least about 20% of a methylvinylidene isomer.

34. The fuel composition according to claim 18, wherein R is amino, $R_1$, $R_2$ and $R_3$ are hydrogen and $R_4$ is a polyalkyl group derived from polyisobutene.

35. The fuel composition according to claim 18, wherein the composition contains from about 50 to about 2,000 parts per million by weight of said compound.

36. The fuel composition according to claim 18, where the composition further contains from about 100 to about 5,000 parts per million by weight of a fuel-soluble, nonvolatile carrier fluid.

37. A fuel concentrate comprising an inert stable oleophilic organic solvent boiling in the range of from about 150° F. to 400° F. and from about 10 to about 70 weight percent of a compound of the formula:

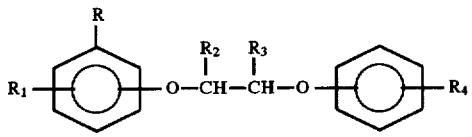

or a fuel soluble salt thereof, wherein R is hydroxy, nitro or —(CH$_2$)$_x$-NR$_5$R$_6$, wherein $R_5$ and $R_6$ are independently hydrogen or lower alkyl having 1 to 6 carbon atoms, and x is 0 or 1;

$R_1$ is hydrogen, hydroxy, nitro or —NR$_7$R$_8$, wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

38. The fuel concentrate according to claim 37, wherein R is nitro, amino or —CH$_2$NH$_2$.

39. The fuel concentrate according to claim 38, wherein R is amino, or —CH$_2$NH$_2$.

40. The fuel concentrate according to claim 39, wherein R is amino.

41. The fuel concentrate according to claim 37, wherein $R_1$ is hydrogen, hydroxy, nitro or amino.

42. The fuel concentrate according to claim 41, wherein $R_1$ is hydrogen or hydroxy.

43. The fuel concentrate according to claim 42, wherein $R_1$ is hydrogen.

44. The fuel concentrate according to claim 37, wherein one of $R_2$ and $R_3$ is hydrogen or lower alkyl of 1 to 4 carbon atoms, and the other is hydrogen.

45. The fuel concentrate according to claim 44, wherein one of $R_2$ and $R_3$ is hydrogen, methyl or ethyl, and the other is hydrogen.

46. The fuel concentrate according to claim 45, wherein $R_2$ is hydrogen, methyl or ethyl, and $R_3$ is hydrogen.

47. The fuel concentrate according to claim 37, wherein $R_4$ is a polyalkyl group having an average molecular weight in the range of about 500 to 3,000.

48. The fuel concentrate according to claim 47, wherein $R_4$ is a polyalkyl group having an average molecular weight in the range of about 700 to 3,000.

49. The fuel concentrate according to claim 48, wherein $R_4$ is a polyalkyl group having an average molecular weight in the range of about 900 to 2,500.

50. The fuel concentrate according to claim 37, wherein $R_4$ is a polyalkyl group derived from polypropylene, polybutene, or a polyalphaolefin oligomer of 1-octene or 1-decene.

51. The fuel concentrate according to claim 50, wherein $R_4$ is a polyalkyl group derived from polyisobutene.

52. The fuel concentrate according to claim 51, wherein the polyisobutene contains at least about 20% of a methylvinylidene isomer.

53. The fuel concentrate according to claim 37, wherein R is amino, $R_1$, $R_2$ and $R_3$ are hydrogen and $R_4$ is a polyalkyl group derived from polyisobutene.

54. The fuel concentrate according to claim 37, wherein the fuel concentrate further contains from about 20 to about 60 weight percent of a fuel-soluble, nonvolatile carrier fluid.

* * * * *